US008119357B2

(12) United States Patent
Amor et al.

(10) Patent No.: US 8,119,357 B2
(45) Date of Patent: Feb. 21, 2012

(54) METHOD FOR ANALYZING A GLYCOMOLECULE

(75) Inventors: Yehudit Amor, Jerusalem (IL); Ofer Markman, Rehovot (IL); Mirit Kolog Gulko, Rishon-Lezion (IL); Albena Samokovlisky, Ashdod (IL); Fredi Kleinman, Rishon le Zion (IL); Tal Alergand, Gedera (IL); Rakefet Rosenfeld, Maccabim (IL); Ruth Maya, Rinatia (IL); Sabina Rebe, Tel Aviv (IL); Idil Kelson Kasuto, Tel Aviv (IL); Haim Bangio, Petach Tiqva (IL)

(73) Assignee: Procognia, Ltd., Ashdod (IL)

( * ) Notice: Subject to any disclaimer, the term of this patent is extended or adjusted under 35 U.S.C. 154(b) by 0 days.

(21) Appl. No.: 12/895,064

(22) Filed: Sep. 30, 2010

(65) Prior Publication Data

US 2011/0021376 A1 Jan. 27, 2011

Related U.S. Application Data

(62) Division of application No. 11/018,077, filed on Dec. 20, 2004, now abandoned.

(60) Provisional application No. 60/531,578, filed on Dec. 18, 2003.

(51) Int. Cl.
*G01N 33/53* (2006.01)
(52) U.S. Cl. .......................................... 435/7.1; 436/518
(58) Field of Classification Search .................. None
See application file for complete search history.

(56) References Cited

U.S. PATENT DOCUMENTS

| | | | |
|---|---|---|---|
| 4,208,479 | A | 6/1980 | Zuk et al. |
| 4,659,659 | A | 4/1987 | Dwek et al. |
| 4,868,292 | A | 9/1989 | Yokoyama et al. |
| 5,229,289 | A | 7/1993 | Kjeldsen et al. |
| 5,646,002 | A | 7/1997 | Linsley et al. |
| 5,719,060 | A | 2/1998 | Hutchens et al. |
| 5,888,757 | A | 3/1999 | Kuranda |
| 5,965,457 | A | 10/1999 | Magnani |
| 6,197,599 | B1 | 3/2001 | Chin et al. |
| 6,323,339 | B1 | 11/2001 | Seeberger et al. |
| 7,056,678 | B1 | 6/2006 | Markman |
| 7,132,251 | B1 | 11/2006 | Markman et al. |

FOREIGN PATENT DOCUMENTS

| | | |
|---|---|---|
| EP | 0166623 A2 | 1/1986 |
| EP | 0421972 A2 | 4/1991 |
| JP | 02032258 A | 2/1990 |
| WO | WO-8805301 A1 | 7/1988 |
| WO | WO-9001938 A1 | 3/1990 |
| WO | WO-9315406 A1 | 8/1993 |
| WO | WO-9322678 A2 | 11/1993 |
| WO | WO-9324503 A1 | 12/1993 |
| WO | WO-9531177 A1 | 11/1995 |
| WO | WO-9735201 A1 | 9/1997 |
| WO | WO-9749989 A2 | 12/1997 |
| WO | WO-9911273 A1 | 3/1999 |
| WO | WO-9918974 A1 | 4/1999 |
| WO | WO-9921588 A1 | 5/1999 |
| WO | WO-9931267 A1 | 6/1999 |
| WO | WO-0068688 A1 | 11/2000 |
| WO | WO-0184147 A1 | 11/2001 |
| WO | WO-0237106 A2 | 5/2002 |

OTHER PUBLICATIONS

Roggentin et al. (Biol. Chem. 1995, vol. 376, p. 569-575).*
Kuster et al. (Analytical Biochem 1997, vol. 250, p. 82-101.*
Alban, et al., "Synthesis of Laminarin Sulfates with Anticoagulant Activity" *Arzneimittel Forschung. Drug Research*, 42(8):1005-1008 (1992).
Andy et al. "The Antigen Identified by A Mouse Monoclonal Antibody Raised Against Human Renal Cancer Cells Is the Adenosine Deaminase Binding Protein." *Biol. Chem.*, 259(20):12844-12849 (1984).
Brenda Search Report, No EC number; V-Labs, Inc. http://www.v-labs.com/sialidase-L.html, 2007.
Chemical Abstracts 105:172905 CA, "Preparation of Oligosaccharides by Gel Filtration Chromatography" *Shengwu Huaxue Zazhi*, 2(3): 69-74 (1986) Abstract Only.
Chemical Abstracts 117:107144, "The Multiple Attack of Endo-1,3-beta-gluconase L-IV From the Marine Mollusk Spisula Sachalinensis III. Evolution of the Total Distribution of Laminarin Hydrolysis Products by Glucanase L-IV and L0.", *Biokhimya*, 57(2):275-278 (1992) Abstract Only.
Chiba, A. et al., "Structures of Sialylated O-Linked Oligosaccharides of Bovine Peripheral Nerve α-Dystroglycan", *The Journal of Biological Chemistry* 272(4):2156-2162 (1997).
Ching, C.K., "Application of Sequential Smith Degradation to Lectin Blots", *Meth. Mol. Med.*, 9(1):147-157 (1998).
Deng et al., "Selection of Antibody Single-Chail Variable Fragments with Improved Carbohydrates Binding by Phage Display", *J. Biol. Chem.*, 269(13):9533-9538 (1994).
Galanina et al. "Determination of Carbohydrate Specificity of Monoclonal Antibodies Against MUC1"*Tumor Biol.*, 19(Suppl. 1):79-87 (1998).
Gattegno et al., "Lectin-Carbohydrate Interactions and Infectivity of Human Immunodeficiency Virus Type 1 (HIV-1)", *AIDS Res. Hum. Retro.*, 8:27-37 (1992).
Goodarzi et al., "A Lectin Method for Investigating the Glycosylation of Nanogram Amounts of Purified Glycoprotein" *Glicoconjugate J.*, 14(4):493-496 (1997).
Hipfner et al., "Membrane Topology of the Multidrug Resistance Protein (MRP); A Study of Glycosylation-Site Mutants Reveals an Extracytosolic $NH_2$ Terminus", *J. Biol. Chem.*, 272:23623-23630 (1997).

(Continued)

*Primary Examiner* — Jacob Cheu
(74) *Attorney, Agent, or Firm* — Mintz Levin Cohn Ferris Glovsky and Popeo, P.C.; David E. Johnson, Esq.; Ivor R. Elrifi

(57) ABSTRACT

The invention relates generally the structural analysis of glycomolecule-containing macromolecules, such as those that occur either attached to proteins (proteoglycans, glycoproteins), lipids, or as free saccharides.

37 Claims, 12 Drawing Sheets

OTHER PUBLICATIONS

Hoja-Lukowics, D. et al., "Affinity Chromatography of Branched Oligosaccharides in Rat Liver β-glucuronidase", *Journal of Homatography*, B755:173-183 (2001).

Hutchinson AM, "Related Articles Characterization of Glycoprotein Oligosaccharides Using Surface Plasmon Resonance", *Anal. Biochem.*, 220(2):303-307 (1994).

Knels et al., "Comparative Structural Analysis of Snail Galactans by a Radioimmunoassay to Elucidate Species-Specific Determinants", *J. Comp. Physiol. B*, 159:629-639 (1989).

Kunkel et al., "Comparisons of the Glycosylation of a Monoclonal Antibody Produced under Nominally Identical Cell Culture Conditions in Two Different Bioreactors" *Biotech. Prog.*, 16:462-470 (2000).

Kuster et al., "Sequencing of N-Linked Oligosaccharides Directly from Protein Gels: In-Gel Deglycosylation Followed by Matrix-Assisted Laser Desorption/Ionization Mass Spectrometry and Normal-Phase High-Performance Liquid Chromatography", *Anal. Biochem.*, 250:82-101 (1997).

Laidler et al., "Arylsulfastase A From Human Placenta Possesses Only High Mannose-type glycans", *Int. J. Biochem. Cell Biol.*, 29(3):475-483 (1997).

Lepagnol-Descamps et al., "Purification and Determination of the Action Pattern of Haliotis Tuberculata Laminarinase", *Carbohydrate Research*, 310(4):283-289 (1998).

Magnani, J., "Immunostaining Free Oligosaccharides Directly on Thin-layer Chromatograms" *Anal. Biochem.*, 150(1):13-17 (1985).

Matsui, T. et al., "Structural Analysis of N-Linked Oligosaccharides of Equine Chorionic Conadotropin and Lutropin β-Subunits", *Biochemistry*, 33:14039-14048 (1994).

Prime, S., et al, "Oligosaccharide Sequencing Based on exo-and Endoglycosidase Digestion and Liquid Chromatographic Analysis of the Products", *Journal of Chromatography A*, 720:263-274 (1996).

Rahman et al. "Monoclonal Antibodies to the Epitope α-gal-(1-4)-β-gal-(1- of Moraxella catarrhalis Ips React With a Similar Epitope in type IV pili of Neisseria Meningitides" *Microbial Pathogenesis*, 24:299-308 (1998).

Read et al. "Analysis of the Structural Heterogeneity of Laminarin by Electrospray-ionisation-mass spectrometry". *Carbohydrate Res.*, 281(2):187-201(1996).

Rosenfeld et al., "U-c Fingerprint: Glycoprotein Analysis Based on A Lectin Array", *Glycobiol.*, 13(11):845 (2003) (Abstract Only).

Sato, Y. et al., "Study of the Sugar Chains of Recombinant Human Amylid Precursor Protein Produced by Chinese Hamster Ovary Cells", *Biochimica et Biophysica Acta*,1472(1-2):344-358 (1999).

Smith et al., "A Novel Sialylfucopentaose in Human Milk", *J. Biol. Chem.*, 262:12040-12047 (1987).

Vanderpuye, OA., et al., "Glycosylation of Membrane Cofactor Protein (CD46) in Human Trophoblast, Kidney and Platelets", *Biochimica. et Biophysica Acta*, 1121:301-308 (1992).

Yamashita et al., "Comparative Studies of the Sugar Chains of Aminopeptidase N and Dipeptidylpeptidase IV Purified From Rat Kidney Brush-border Membrane" *Biochem.*, 27(15):5565-5573 (1988).

Yamahita et al., "Charachteristics of Asparagine-linked Sugar Chains of Spingolipied Activator Protein 1 Purified Form Normal Human Liver and GM1 Gangliosidosis (type 1) Liver" Biochem, 29(12):3030-3039 (1990).

\* cited by examiner

METHOD FOR ANALYZING A GLYCOMOLECULE

RELATED APPLICATIONS

This application is a divisional application of U.S. Ser. No. 11/018,077, filed Dec. 20, 2004 and claims the benefit of, and priority to, U.S. Ser. No. 60/531,578, filed Dec. 18, 2003. The contents of which are each incorporated herein by reference in their entirety.

FIELD OF THE INVENTION

The invention relates generally to the structural analysis of glycomolecules, which are molecules that contain carbohydrates and include carbohydrates attached to proteins (proteoglycans, glycoproteins), to lipids, or carbohydrates present as free polysaccharides.

BACKGROUND OF THE INVENTION

Mammalian glycoprotein oligosaccharides are commonly built from a limited number of monosaccharides. Nevertheless, structural diversity is vast, mainly due to complex branching patterns. Glycosylation sites on glycoproteins commonly display microheterogeneity in that they can be fully or partially occupied by structurally diverse oligosaccharides. Consequently, a glycoprotein is not typically isolated as a single structural entity, but rather as a set of glycosylation variants known as glycoforms.

There is evidence that both the in vivo and in vitro properties of glycoproteins are affected by changes in occupancy and/or the precise oligosaccharide attached to a particular site. Distinct biological properties have been correlated with the presence of particular glycoforms.

A method for determining the composition and sequence of polysaccharides in a carbohydrate-containing molecule ("glycomolecule") has been described (see, e.g., WO00/668688, WO01/84147, WO02/37106, and WO02/44714). In this method, termed UC-FINGERPRINT™ analysis (also known as GMID™ analysis), a carbohydrate-containing molecule is added to a substrate containing an array of saccharide-binding agents (typically antibodies or lectins). Saccharide-binding agents bound to the glycomolecule are identified, and the binding information is used to obtain composition and sequence information of the monosaccharide subunits in the polysaccharide.

SUMMARY OF THE INVENTION

The invention is based in part on the discovery of methods that facilitate the preparation of glycomolecules for subsequent analysis in UC-FINGERPRINT™ technology. The analysis provides glycan composition and sequence information, which is often referred to as a fingerprint of the glycomolecule.

Among the advantages of the method is simplified sample preparation and processing. The methods described herein eliminate the need for multiple pretreatment, treatment, purification, and buffer changing steps. In addition, the methods facilitate access to glycomolecules that are otherwise difficult to analyze. These glycans include, e.g., glycans in inter-subunit clefts or intra-subunit clefts of glycoproteins.

In one aspect, the invention provides a method for determining a glycomolecule fingerprint for a glycomolecule. In some embodiments, the glycomolecule is one whose native glycan structure has been modified. The method includes adding the glycomolecule to a substrate that includes a plurality of saccharide-binding agents. Glycomolecules bound to saccharide-binding agents on the substrate are detected. A fingerprint is obtained for the glycomolecule based on the binding of the glycomolecule to the saccharide-binding agents.

In some embodiments, the glycomolecule has been modified by desialylation. The extent of the desialylation can be modulated, so that in some embodiments, substantially all of the sialic acid residues have been removed from the glycomolecule. In other embodiments, less than all of the sialic acids have been removed from the glycomolecule.

A suitable method for desialylating the glycomolecule is by reacting the glycomolecule with a sialidase. The glycomolecule can optionally be reacted with the sialidase in the presence of a protease inhibitor.

The glycomolecule can alternatively, or in addition, be modified by treatment with PNGaseF. The extent of treatment with PNGaseF can be modulated, so that in some embodiments, substantially all of the bonds between the innermost GlcNAc and asparagine residues of high mannose, hybrid and complex oligosaccharides of the glycoprotein have been cleaved. In other embodiments, less than all of the N-Acetyl Glucosamine acid residues have been cleaved.

In some embodiments, the method includes reacting the glycomolecule with a reducing agent and, preferably, an alkylating agent prior to obtaining the fingerprint. Examples of suitable reducing agents include mercaptoethanol, dithiothreitol, and mercaptethylamine. Examples of suitable alkylating agents iodoacetamide and iodoacetic acid.

In some embodiments, all steps of the method are performed in a single container.

In some embodiments, the glycomolecule is detected with a label associated with the glycomolecule. Examples of suitable labels include, e.g., a fluorescent label. The fluorescent label can be, e.g., fluorescein isothiocyanate (FITC), rhodamine, Texas Red, and Cy5.

The label can be added to the glycomolecule prior to, after, or while adding the glycomolecule to the substrate.

In some embodiments, the label is associated directly with the glycomolecule. In other embodiments, the label is associated with a second saccharide-binding agent that binds specifically to the glycomolecule. The second saccharide-binding agent can be, e.g., a lectin or an antibody. In some embodiments, the label is associated with an agent (such as an antibody) that binds specifically to a non-carbohydrate region of the glycomolecule.

In some embodiments, the method further includes purifying the glycomolecule prior to adding the glycomolecule to the substrate. The purification can be, e.g., by column chromatography ordialysis with a molecular cut off of a defined mass, e.g., 5000 kD The glycomolecule can be any saccharide-containing molecule. Examples include glycoprotein, polysaccharide, or glycolipid.

In some embodiments, the glycoprotein is obtained from a cell culture medium. In some embodiments, the glycoprotein is purified and/or concentrated prior to being used. In other embodiments the glycoprotein is obtained from the medium and used without purification or concentration.

In some embodiments, the method includes treating the glycomolecule with a detergent prior to obtaining the fingerprint. The detergent can be, e.g., a non-ionic detergent or anionic detergent. Examples of a suitable detergent include, e.g. sodium docecyl sulfate (SDS), Triton, and Tween80.

Examples of suitable glycoproteins include, eg., immunuglobuin molecules (including IgA, IgD, or IgG, or IgM isotypes) or fragments of immunoglobulin molecules. For example, the fragment can include an Fc region of an immunoglobulin.

In another aspect, the invention provides a kit that includes a glycomolecule modification agent selected that is a desialidase and/or a PNGase F, a labeling agent for labeling a glycomolecule, a container and, optionally instructions for using the kit to modify the glycomolecule The directions can be provided on a kit label or as a kit insert, which describe how to manipulate a glycomolecule using the methods described herein.

The kit may additionally contain a plurality of saccharide-binding agents, a reducing agent, a detergent and an alkylating agent. The labeling agent may bind directly to the glycomolecule. Alternatively, the labeling agent is present with, or capable of being associated with, a second saccharide-binding agent that binds to the glycomolecule. The second saccharide-binding agent can be, e.g., a lectin or an antibody.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. These include, but are not limited to, WO00/68688, WO01/84147, WO02/37106, and WO02/44714. In the case of conflict, the present Specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1C shows fingerprints of the same hmLF sample following gradual enzymatic trimming of the glycans. Cross-hatched, native hmLF; dark shading, hmLF following de-sialylalation; dark shading, hmLF following removal of terminal galactose residues; open, hmLF following removal of terminal GlcNAc.

DETAILED DESCRIPTION OF THE INVENTION

Figure 1A:
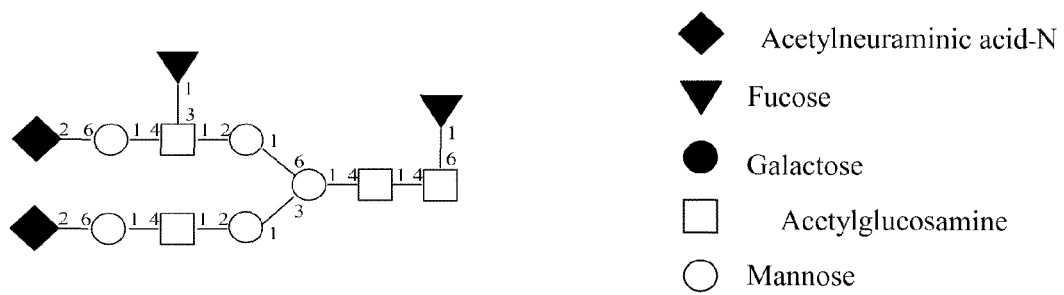
FIG. 1A is a schematic diagram showing the representative bi-antennary glycans of human milk lactoferrin (hmLF). The various glycans differ in the presence of the (2,6) linked sialic acid residues and the (1,3) linked antennary fucose.

The invention provides methods for determining the glycan composition and sequence of carbohydrate-containing molecules. In some embodiments, the methods include modifying a glycomolecule. These methods enhance the information obtained when the carbohydrate content of the carbohydrate-containing molecule is analyzed.

The methods for analyzing the glycomolecule are particularly suited for analyzing molecules in the UC-FINGERPRINT™ method, which is also referred to as a glycomolecule identification (GMID™) method. In this method, information about the carbohydrate content of a glycomolecule is obtained by adding a glycomolecule to a substrate to which is attached one or more saccharide-binding agents (also referred to herein as first saccharide-binding agents). The first saccharide-binding agents that have bound the glycomolecule are identified, and the resulting binding information is used to generate a fingerprint of the glycomolecule.

For example, one way to perform the method is with a set of 20-30 lectins printed on a membrane-coated glass slide in replicates of 4-8. A sample of intact glycoprotein is applied to the array, and its binding pattern is detected by either direct labeling of the glycoprotein using FITC, or by using an FITC-labeled probe that is directed at either the protein moiety—an antibody for example, or a carbohydrate moiety—a lectin. The resulting fingerprints are highly characteristic of the glycosylation pattern of the sample. The large number of lectins, each with its specific recognition pattern, ensures high sensitivity of the fingerprint to changes in the glycosylation pattern. Other fluorescent labels such as Cy3 Cy5 can also be used. In addition, labeling can be effected using biotin-avidin systems known in the art.

Modifications of Glycomolecules Prior to Fingerprinting Analysis

It has now been unexpectedly found that the modifications describe herein enhance the type and amount of information that can be obtained in UC-FINGERPRINT™ analysis. One modification is removing some or all of the sialic acid residues from glycomolecule, a process know as desialylation, prior to UC-FINGERPRINT™ analysis. Sialic acid residues are negatively charged residues that cap carbohydrate moieties attached to many sites on glycoproteins. Sialic acid residues can be removed using the enzyme sialidase, which is also known as neuraminidase. The extent of desialylation can be controlled by modulating the extent of digestion of the glycomolecule with the sialidase. In addition to sialidase, any other method that reduces the sialic acid content of a glycomolecule (including a glycoprotein) can be used.

Another modification that has been found to enhance the information revealed in a UC-FINGERPRINT™ analysis is digestion with PNGaseF, which is also known as N-glycosidase F. PNGase F cleaves N-linked glycoproteins between the innermost GlcNAc and asparagine residues of high mannose, hybrid and complex oligosaccharides. O-linked glycan residues (such as N-GlcNAc and O-Fuc) are not affected and are available for subsequent analysis. This modification is particularly suitable glycoproteins for which O-linked glycan composition is of interest. An example of such a protein is erythropoietin (EPO).

In addition to PNGaseF, a glycomolecule can be modified with other glycosidase-modifying anzymes known in the art, e.g., Endo F2, Endo F3, Endo H.

A further modification for preparing a glycomolecule for UC-FINGERPRINT™ analysis is to expose the glycomolecule to a reducing agent and, alkylating agent. Exposure to a reducing agent can disrupt intra- and inter-chain disulfide bonds and make available for analysis glycans that would not otherwise be detected. Suitable reducing agents include, e.g., β-mercaptoethanol, dithiothreitol, and mercaptethylamine. Alkylating agents include, e.g., iodoacetamide and iodoacetic acid.

A still further modification that has been found to enhance the information obtained by UC-FINGERPRINT™ analysis is to subject the glycomolecule to denaturing conditions. This modification is suitable for glycomolecules containing glycans that are hidden or obscured because of, e.g., protein aggregation. For example, a glycoprotein can be heated in the presence of a detergent prior to performing UC-FINGERPRINT™ analysis. The optimal conditions (including, e.g., selection of detergent, temperature, buffer composition and concentration, and pH) can be chosen based on the glycomolecule of interest, the first saccharide-binding agents that are immobilized on the substrate, and/or the labeling scheme that is used to detect glycomolecules bound to the saccharide-binding agents on the substrate.

For example, to detect glycans associated with Fc subunits for IgG molecules, the glycoprotein can be treated in 0.01 to 075% SDS, more preferably 0.04-0.06% SDS, and most preferably about 0.05% SDS. The sample is in addition boiled for 5-15 minutes at 95-100° C., e.g., at 10 minutes at 100° C., or the equivalent.

The above-described modifications can be performed singly or in any desired combination. For example, a glycoprotein can be treated with salidase, and then subjected to reducing conditions prior to submitting the modified glycoprotein to UC-FINGERPRINT™ analysis.

The methods described above facilitate identification of carbohydrate information for glycoproteins that contain glycans that are obscured by sialic acid residues, and/or obscured because the glycoproteins otherwise exist as present as multimers and for are present in inter-subunit or intra-subunit clefts.

It has been further unexpectedly discovered that many of the manipulations described herein—modification, labeling, and reducing, for example—can be performed without the need for changing the buffer. This eliminates the need to subject a glycomolecule of interest to cumbersome, multi-step processing treatments. In addition, the method can be performed using less material, with less material loss and in a shorter time.

If desired, the modifications described above can be performed directly on glycomolecules (including glycoproteins) isolated directly from a culture medium.

Determining Fingerprints of Modified Glycomolecules

A "glycomolecule fingerprint" refers to the information provided by the amount of binding detected to one or more saccharide-binding agents for a glycomolecule of interest. The fingerprint can be expressed graphically by presenting as a histogram the relative binding intensities for multiple saccharide-binding agents. In some embodiments, the analysis of the glycomolecule includes determining a map of the glycomolecule. "Mapping"-means defining a sequential order of certain predefined patterns on the polysaccharide chain. The predefined patterns can correspond to of location(s) on the glycomolecule that bind to a saccharide-binding agent, and/or are substrates for a glycoside-cleaving enzyme.

A glycomolecule can include any molecule that includes a saccharide moiety. For example, a glycomolecule can includes carbohydrate-containing proteins (glycoproteins) or glycolipids, and free polysaccharides. Glycoproetins include, e.g., fetuin, $\alpha_1$ Acid GP, and tPA.

The modified glycomolecules are added to a substrate that includes one or more first saccharide-binding agents. The first saccharide-binding agent may be immobilized to a substrate using any art-recognized method. For example, immobilization may utilize functional groups of the protein, such as amino, carboxy, hydroxyl, or thiol groups. For instance, a glass support may be functionalized with an epode group by reaction with silane. The epode group reacts with amino groups such as the free s-amino groups of lysine residues. Another mechanism consists in covering a surface with electrophilic materials such as gold. As such materials form stable conjugates with thiol groups, a protein may be linked to such materials directly by free thiol groups of cysteine residues. Alternatively, thiol groups may be introduced into the protein by conventional chemistry, or by reaction with a molecule that contains one or more thiol groups and a group reacting with free amino groups, such as the N-hydroxyl succinimidyl ester of cysteine. Also thiol-cleavable cross-linkers, such as dithiobis(succinimidyl propionate) may be reacted with amino groups of a protein. A reduction with sulfhydryl agent will then expose free thiol groups of the cross-linker.

For some applications, it is preferable to design a substrate that contains a plurality of saccharide-binding agents known to bind, or suspected of binding, to a particular glycomolecule of interest. For example, heparin, heparin sulfate, or fragments (such as those produced by heparanase digestion), as well as variant forms of these polysaccharides can be screened for their ability to bind to one or more proteins such as, e.g., αFGF, βFGF, PDGF, VEGF, VEGF-R, HGF, EGF, TGF-beta, MCP-1, -2 and -3, IL-1, -2, -3, -6, -7, -8, -10, and -12, annexin IV, V, and VI, MIP-1 alpha, MIP-1 beta, ecotaxin, thrombospondin, PF-4, IP-10, interferon alpha, interferon gamma, selectin L and selectin P, antithrombin, plasminogen activator, vitronectin, CD44, SOD, lipoprotein lipase, ApoE, fibronectin, and laminin. These putative agents can be attached to a surface (i.e., can be first saccharide binding agents).

The substrate can be conveniently provided on a membrane disposed on a supporting surface. For example, the saccharide-binding agents can be provided on a nitrocellulose filter on a glass slide. Alternatively, the substrate can be a microsphere, or bead. In various embodiments, one or more distinct saccharide-binding agents are provided on a single microsphere.

Saccharide-Binding Agents

A suitable saccharide-binding agent is any agent that binds specifically to a carbohydrate-portion of a glycomolecule. Suitable saccharide-binding agents include, e.g., lectins, antibodies that recognize carbohydrate-containing epitopes, and carbohydrate-modifying enzymes, such as glycosidases.

Lectins are proteins isolated from plants that bind saccharides. For the purpose of this application, the term "lectin" also encompasses saccharide-binding proteins from animal species (e.g. "mammalian lectins"). Examples of lectins include lectins isolated from the following plants: *Conavalia ensiformis, Anguilla anguilla, Tritium vulgaris, Datura stramonium, Galnthus nivalis, Maackia amurensis, Arachis hypogaea, Sambucus nigra, Erythtina cristagalli, Sambucis nigra, Erythrina cristagalli, Lens culinaris, Glycine max, Phaseolus vulgaris Allomyrina dichotoma, Dolichos biflorus, Lotus tetragonolobus, Ulex europaeus*, and *Ricinus commurcis*. Other biologically active compounds such as cytokines, chemokines and growth factors also bind glycomolecules, and hence, for the purposes of the present invention are considered to be lectins.

Examples of glycosidases include a-Galactosidase, (3-Galactosidase, N-acetylhexosaminidase, α-mannosidase, β-mannosidase, and α-Fucosidase.

Detecting Bound Glycomolecules

Glycomolecules that have bound to a saccharide-binding agent on a substrate can be detected using any method that will result in detection of the bound glycomolecule. For example, the glycomolecule can be directly labeled before, during, or after it is added to the substrate. Examples of direct labeling include, e.g., FITC labeling.

Alternatively, the bound glycomolecule can be detected with a label associated with an agent that specifically recognizes the bound glycomolecule. The agent can recognize a carbohydrate-containing region of the molecule. When the agent has this specificity it is referred to as a second saccharide-binding agent. The second saccharide-binding agent can be an antibody or a lectin, including the antibodies and lectins described above.

In some embodiments, the agent recognizes a non-carbohydrate portion of the glycomolecule. An example of such an agent is an antibody that recognizes a peptide epitope in a glycoprotein.

If desired, bound glycomolecules can be detected using a series of agents. For example, desialo darbepoetin alfa (ARASNEP™) bound to glycans can be detected using anti-human EPO monoclonal mouse antibody followed by an anti-mouse IgG-FITC-labeled antibody.

The label can be any label that is detected, or is capable of being detected. Examples of suitable labels include, e.g., chromogenic label, a radiolabel, a fluorescent label, and a biotinylated label. Thus, the label can be, e.g., colored lectins, fluorescent lectins, biotin-labeled lectins, fluorescent labels, fluorescent antibodies, biotin-labeled antibodies, and enzyme-labeled antibodies. In preferred embodiments, the label is a chromogenic label. The term "chromogenic binding agent" includes all agents that bind to saccharides and which have a distinct color or otherwise detectable marker, such that following binding to a saccharide, the saccharide acquires the color or other marker. In addition to chemical structures having intrinsic, readily-observable colors in the visible range, other markers used include fluorescent groups, biotin tags, enzymes (that may be used in a reaction that results in the formation of a colored product), magnetic and isotopic markers, and so on. The foregoing list of detectable markers is for illustrative purposes only, and is in no way intended to be limiting or exhaustive. In a similar vein, the term "color" as used herein (e.g. in the context of step (e) of the above described method) also includes any detectable marker.

The label may be attached to the agent using methods known in the art. Labels include any detectable group attached to the glycomolecule, or detection agent that does not interfere with its function. Labels may be enzymes, such as peroxidase and phosphatase. In principle, also enzymes such as glucose oxidase and β-galactosidase could be used. It must then be taken into account that the saccharide may be modified if it contains the monosaccharide units that react with such enzymes. Further labels that may be used include fluorescent labels, such as Fluorescein, Texas Red, Lucifer Yellow, Rhodamine, Nile-red, tetramethyl-rhodamine-5-isothiocyanate, 1,6-diphenyl-1,3,5-hexatriene, cis-Parinaric acid, Phycoerythrin, Allophycocyanin, 4',6-diamidino-2-phenylindole (DAPI), Hoechst 33258, 2-aminobenzamide, and the like. Further labels include electron dense metals, such as gold, ligands, haptens, such as biotin, radioactive labels.

The agent can additionally be detected using enzymatic labels. The detection of enzymatic labels is well known in the art. Examples include, e.g., ELISA and other techniques where enzymatic detection is routinely used. The enzymes are available commercially, e.g., from companies such as Pierce.

In some embodiments, the label is detected using fluorescent labels. Fluorescent labels require an excitation at a certain wavelength and detection at a different wavelength. The methods for fluorescent detection are well known in the art and have been published in many articles and textbooks. A selection of publications on this topic can be found at p. O-124 to O-126 in the 1994 catalog of Pierce. Fluorescent labels are commercially available from Companies such as SIGMA, or the above-noted Pierce catalog.

The agent may itself contain a carbohydrate moiety and/or protein. Coupling labels to proteins and sugars are techniques well known in the art. For instance, commercial kits for labeling saccharides with fluorescent or radioactive labels are available from Oxford Glycosystems, Abingdon, UK, and ProZyme, San Leandro, Calif. USA). Reagents and instructions for their use for labeling proteins are available from the above-noted Pierce catalog.

Coupling is usually carried out by using functional groups, such as hydroxyl, aldehyde, keto, amino, sulfhydryl, carboxylic acid, or the like groups. A number of labels, such as fluorescent labels, are commercially available that react with these groups. In addition, bifunctional cross-linkers that react with the label on one side and with the protein or saccharide on the other may be employed. The use of cross-linkers may be advantageous in order to avoid loss of function of the protein or saccharide.

While the labeling has been described with respect to modified glycomolecules, the invention also encompasses these labeling methods when used to perform UC-FINGERPRINT™ analysis of unmodified glycomolecules.

Obtaining a Fingerprint

The intensity of label associated with bound glycomolecules can be detected using methods known in the art. Some detection methods are described in WO 93/22678. Particularly suitable for the method of the present invention is the CCD detector method. This method may be used in combination with labels that absorb light at certain frequencies, and so block the path of a test light source to the VLSI surface, so that the CCD sensors detect a diminished light quantity in the area where the labeled agent has bound. The method may also be used with fluorescent labels, making use of the fact that such labels absorb light at the excitation frequency. Alternatively, the CCD sensors may be used to detect the emission of the fluorescent label, after excitation. Separation of the emission signal from the excitation light may be achieved either by using sensors with different sensitivities for the different wavelengths, or by temporal resolution, or a combination of both.

The fingerprint is preferably determined by correcting for the glucose concentration of the media from which the glycomolecule is taken.

The acquired binding information can be used directly, e.g., following visual inspection of the binding pattern. Alternatively, the binding information can be stored, e.g., as a photograph or digitized image. If desired, the binding information can be stored in a database. Interpretation of binding information is also discussed in, e.g., WO00/68688, WO01/84147, WO02/37106, and WO02/44714, the contents of which are incorporated by reference herein in their entirety.

Kits

The invention additionally provides kits for modifying glycomolecules and then subjecting them to UC-FINGERPRINT™ analysis. The contents of a kit can include One or more of a modification agent(s), a labeling reagent for detecting a glycomolecule that is bound to a saccharide-binding agent, and, if desired, a substrate that contains or is capable of attaching to one or more saccharide-binding agents. The substrate can be, e.g., a microsphere.

Each kit preferably includes saccharide-binding agent or agents. The reagent is preferably supplied in a solid form or liquid buffer that is suitable for inventory storage, and later for exchange or addition into the reaction medium when the test is performed. Suitable packaging is provided. The kit may optionally provide additional components that are useful in the procedure. These optional components include buffers, capture reagents, developing reagents, labels, reacting surfaces, means for detection, control samples, instructions, and interpretive information.

The kit may optionally include a detectable second saccharide-binding agent and, if desired, reagents of detecting the second binding agent. The plurality of first saccharide-binding agents is preferably attached at predetermined location on the substrate and a detectable second saccharide-binding agent. In other embodiments, the kit is provided with a substrate and first saccharide-binding agents that can be attached to the substrate, as well as second saccharide-binding agents.

Figure 6:
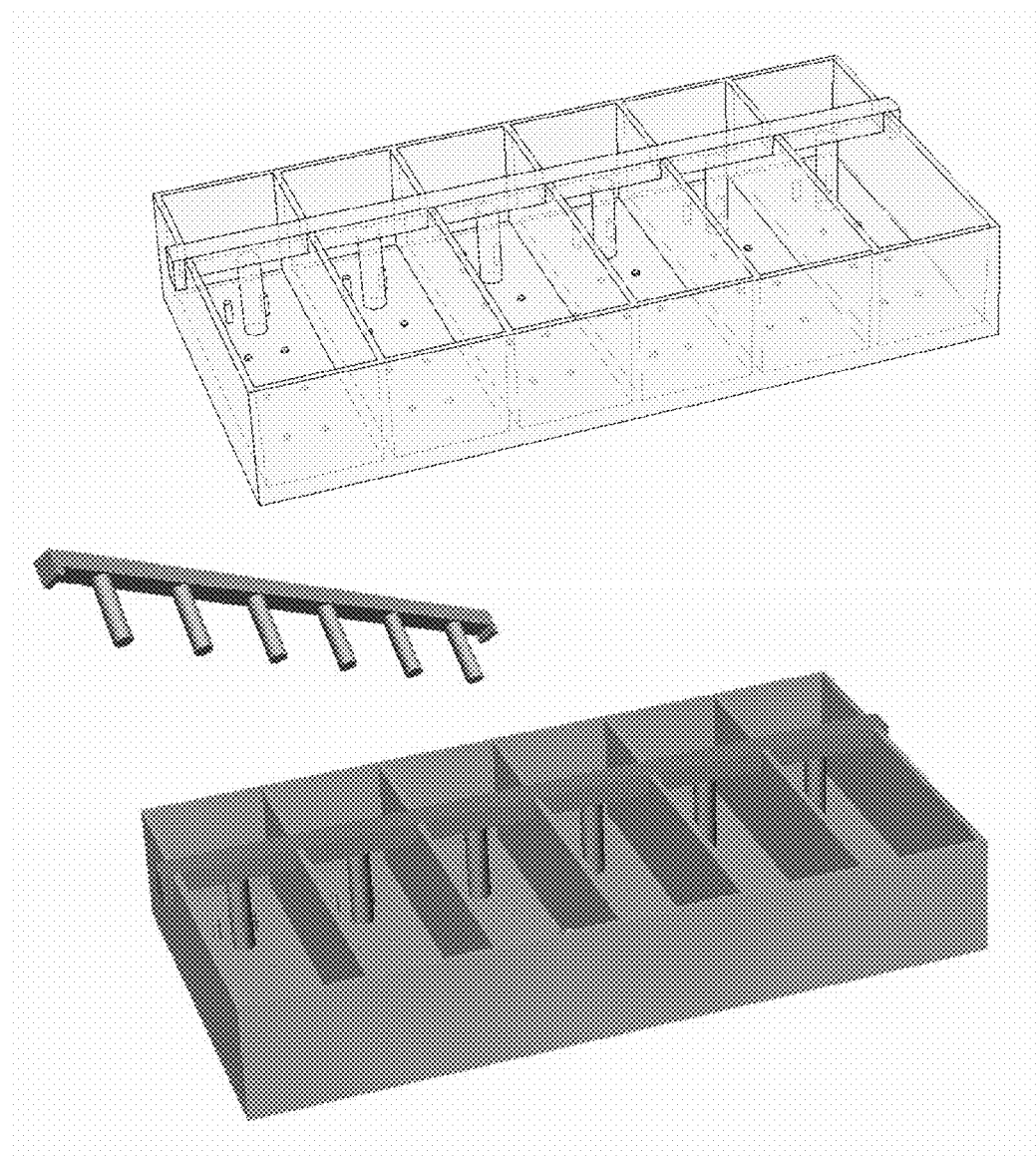
FIG. 6 is a representation of a manual holder for a slide wash.

If desired, a slide holder as shown in FIG. 6 may be included in the kit. The holder is divided to chambers in a size slightly bigger then a standard microscope slide, with a proper space to reach with a gloved finger, the slide is held by stoppers to prevent forward-backward and side movement, and its bottom is equipped with bumps to avoid the formation of vacuum and laminar forces between the slide and the chamber bottom. Each chamber can typically hold 5-10 ml of liquid and is by thus a vessel for slide wash and incubation. A cover holder with typical feet reach the holding surface of the slides and by thus allows to flip the chambers and discard liquids in a more effective way.

The invention will be further illustrated in the following non-limiting examples.

Example 1

Comparative Glycomolecule Fingerprints of Desialized and Non-Desialized Glycoproteins The glycomolecule fingerprint of human milk lactoferrin (hmLF) before and after disialyzation was examined. hmLF is a glycoprotein with a relatively simple glycosylation structure (Spik et al. Eur J Biochem. 1982; 121(2):413-9). The hmLF structure includes two glycosylation sites that are occupied by any of 5 major glycans, resulting in 25 possible glycoforms. All of these glycans are of the complex bi-antennary type, containing a core fucose and differing in their levels of sialylation and the variable presence of antennary fucose (FIG. 1A). The various glycans differ in the presence of the (2,6) linked sialic acid residues and the (1,3) linked antennary fucose.

Figure 1B:
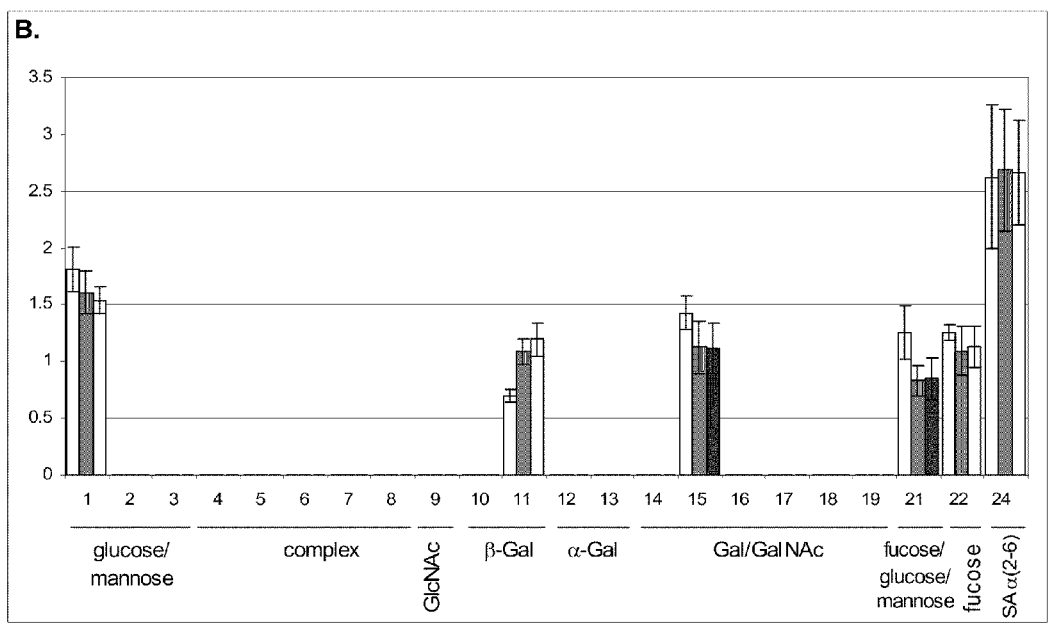
FIGS. 1B and 1C are fingerprints obtained by using a labeled anti-lactoferrin antibody as a probe. Twenty-four array-bound lectins were used in these experiments, and are grouped by their specificities on the abscissa. The group of complex N-linked glycans contains lectins that do not bind to monosaccharides, but rather require a complex N-linked glycan containing at least 3 antennae; Results are shown for three independent experiments. Signals were corrected for differences in scanning parameters (laser power and PMT gain) for each slide, if applicable, and for differences in levels of probe fluorescence if these differ between experiments.

The fingerprints (FIG. 1B and FIG. 1C) were obtained by using a labeled anti-lactoferrin antibody as a probe. Twenty-four array-bound lectins were used and are grouped by their specificities on the abscissa. The group of complex N-linked glycans contains lectins that do not bind to monosaccharides, but rather require a complex N-linked glycan containing at least 3 antennae; the data summarized in FIG. 1B are the result of three independent experiments. Signals are corrected for differences in scanning parameters (laser power and PMT gain) for each slide, if applicable, and for differences in levels of probe fluorescence if these differ between experiments. Lectins were printed on a membrane-coated glass slide in replicates of 4-8. Lectins were purchased from Vector Laboratories (Burlingame, Calif.). The lectins were dissolved in PBS at pH 7.4 to concentrations of 2-4 mg/ml. Lectins are spotted with a high precision robot for microarray spotting (MicroGrid, Biorobotics, Cambridge, UK) onto nitrocellulose coated glass slides (FAST Slides, Schleicher & Schull, Keene, N.H.), using solid pins of 0.4 mm diameter, at a center-to-center distance of 0.9 mm. Arrays were blocked with 1% BSA (Sigma). Samples are incubated with PBS buffer containing 1 mM CaCl, 1 mM MgCl and 0.1 mM MnCl followed by a wash using the same buffer. The process was fully automated on the Protein Array Workstation (Perkin Elmer, Wellesley, Mass.). HmLF was applied to the array and its binding pattern was detected by scanning with a confocal laser scanner (ScannArray Express, Perkin Elmer), and data analyzed using the ArrayPro software package (Media Cybernetics, Silver Spring, Md.).

FIG. 1B shows fingerprints of hmLF obtained with a labeled anti-lactoferrin antibody probe. A polyclonal anti-hmLF antibody was used to detect hmLF bound to the immobilized lectins. The polyclonal antibody recognizes all hmLF glycoforms, and thus each bar in the histogram represents the binding observed on one of the array-bound lectins, which are grouped by their specificities. Three independent experiments are depicted, demonstrating the reproducibility of the platform. A relatively simple fingerprint, containing few signals, is observed: one major signal arises from a lectin from the mannose/glucose specificity group, and no signals are observed in the complex glycan specificity group, which recognize tri- and higher order antennary structures. These results indicate that all of the lactoferrin glycans are of the complex bi-antennary type. Two signals arise from lectins that recognize the terminal galactose of non-sialylated antennae, one from the Gal specificity group and another from the Gal/GalNAc group, and additional signals arise from two lectins that recognize fucose (both core and antennary), and from a lectin recognizing the sialic acid.

10 mg/ml of hmLactoferrin was desialylated using 50 mU/ml Neuraminidase from *Arthrobacter ureafaciens* (Roche cat #269611). Galactose was removed using 20 mU/ml beta 1,4-Galactosidase from *Streptococcus pneumoniae* (Calbiochem, cat #345806). N-acetylglucosamine was removed with 20 U/ml of beta 1-2,3,4,6-N-Acetylglucosaminidase from *Streptococcus pneumoniae* (Calbiochem cat #110116). All cleavage reactions were performed in the present of 50 mM phosphate buffer at pH 6 containing protease inhibitors (PI Cocktail Set I-Calbiochem cat #539131) for 19 hours at 37° C.

Figure 1C:
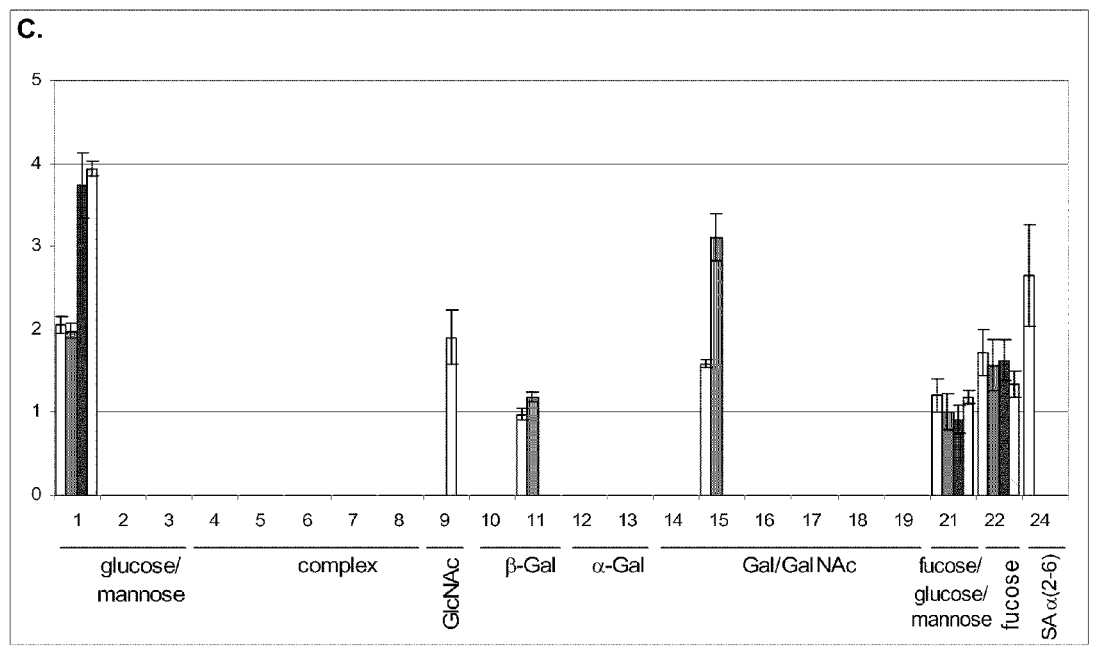

FIG. 1C depicts fingerprints of hmLF following successive enzymatic trimming of the glycans, and using the same antibody probe. FIG. 1C shows the fingerprints of the same hmLF sample following gradual enzymatic trimming of the glycans (KEY—native hmLF (box with diagonal lines); following de-sialylalation (dark shaded box); following removal of terminal galactose residues (light shaded box); following removal of terminal GlcNAc (clear box)).

The fingerprint of the native sample is virtually identical to that observed in the experiments of FIG. 1B. Following desialylation, signals from the lectin of the glucose/mannose specificity group, which recognizes the complex bi-antennary core, and those from the fucose-recognizing lectins remain virtually unchanged, while the signals from the sialic-acid recognizing lectin disappear. These outcomes are expected in light of what is known about the structure of hmLF glycans.

The galactose-recognizing lectins demonstrate a more complex behavior. The signals from these lectins increase differentially, demonstrating the differential sensitivity of these lectins to the presence of sialic acid: lectin 11 is able to bind the non-sialylated antenna of a mono-sialylated glycan and thus the small increase in signal from this lectin following desialylation indicates a low level of di-sialylated structures in the native sample. In contrast, the affinity of lectin 15 towards mono-sialylated glycans is significantly decreased in comparison to fully desialylated glycans, and thus the large increase in the signal of this lectin indicates that the native protein contains a low level of neutral glycans. In addition, the large difference in the signals observed on these lectins in response to the desialylated sample demonstrates that their affinity towards galactose differs significantly.

The signal from lectin 1 increases following the removal of the terminal-galactose, demonstrating increased accessibility of the lectin to the tri-mannosyl core. The signals from the galactose recognizing lectins disappear, and a signal from a lectin that recognizes the newly exposed terminal N-acetylglucosamine (GlcNAc) is evident. The signals from the fucose recognizing lectins remain unchanged. Following the removal of the GlcNAc only the signals from lectin 1, recognizing the tri-mannosyl core, and from the fucose recognizing lectins are observed.

These results clearly demonstrate the sensitivity of the bound lectins to changes in the glycan structures. The fingerprints of FIGS. 1B and 1C also demonstrate the complexity of deconvoluting the fingerprints: signal intensities do not correlate with the abundance of the recognized epitopes. The abovementioned example of lectins 11 and 15 having different affinities for the terminal galactose of the desialylated antennae illustrate this; an additional example is revealed by comparing the signals of lectins 21 and 22. Lectin 21 recognizes the core fucose, which is present in all of the lactoferrin glycans, whereas lectin 22, whose signal is 40% higher than that of lectin 21, recognizes the antennary fucose present on only approximately 30% of the glycans. Thus quantification of the glycan epitopes requires a comprehensive understanding of the lectin glycan recognition.

Example 2

Rule-Based Fingerprint Deconvolution

Deconvolution of the fingerprints is optimally performed by acquiring a detailed understanding of lectin glycan recognition. This is complicated by the broadness of lectin specificities towards glycans, and by the fact that the affinities, both within and between the groups, differ markedly and are unknown. Measurement of these affinities are hampered by the inability to obtain a single-glycan-type glycoprotein for each glycan type. Mathematically, this translates into uncertainties in the conditional probabilities of observing a signal for a particular lectin, when the presence of a particular glycan is known. This limits the use of probabilistic-based algorithms.

An alternative approach using a rule-based expert system (Castillo et al., "Expert Systems and Probabilistic Network Models"-(Monographs in Computer Science) Springer-Verlag, New-York 1997) for fingerprint deconvolution was chosen. The rule base consists of lectin-glycan recognition rules that were extracted from the literature and further refined by manual curation of fingerprints that were run on a large set of well-characterized glycoproteins. Examples of these rules include:

if (LEC1) then (Tri-antennary, Tetra-antennary)  (1)

if (LEC2) then (Hybrid, Tri-antennary, Tetra-antennary)  (2)

if (LEC3|(LEC3>>LEC2) AND (LEC4, LEC5)) then (High mannose)  (3)

The rules are written in a natural language form and are thus easily edited and optimized. In the example above, LEC1-LEC5 represent particular lectins; the first rule reads "if a signal is observed on LEC1 then there is either a tri-antennary or a tetra-antennary glycan present in the sample". As emphasized above, knowledge of the relative probabilities of each of these epitopes is not available, and thus a straightforward inference from the set of rules relevant for any particular fingerprint is not possible.

The algorithmic solution adopted is an inference engine based on the Dempster-Shafer theory of evidence (Shafer, Probability judgment in artificial intelligence. In L. N. Kanal and J. F. Lemmer, editors, Uncertainty in Artificial Intelligence. North-Holland, New-York, 1986; Lefevre et al. A Generic Framework for Resolving the Conflict in the Combination of Belief Structures. FUSION 2000—3rd International Conference on Information Fusion. July 2000, Paris, France; Ronald R. Yager (Editor), Janusz Kacprzyk (Editor), Mario Fedrizzi (Editor). Advances in the Dempster-Shafer Theory of Evidence. Wiley & Sons 1994). This framework is powerful in situations where many pieces of evidence (observations) must be weighted in order to determine a single most probable model, and there is uncertainty in the system. Here, the lectin signals are the pieces of evidence, having uncertainties that stem from the broad specificities of the lectins as well as the multiplicity of glycans, glycoforms, and lectin recognition epitopes. The inputs to the inference engine are the lectin binding signals (the fingerprint) and the set of interpretation rules. The inference engine translates the rules into "evidence" based on signal intensities. The three rules shown in the example above are translated into:

Evidence(Tri-antennary, Tetra-antennary)=Signal (LEC1)  (1)

Evidence(Hybrid, Tri-antennary, Tetra-antennary)= Signal(LEC2)  (2)

accordance with convention, N-linked and O-linked glycans distributions were treated independently; the overall ratio of N/O-linked glycans is directly estimated from the relative intensities of the signals obtained from N-linked glycan and O-linked glycan specific lectins. *** indicates an estimate of average level of sialylated glycans. A comparison of observed values to values compiled from the literature and verified by mass-spectroscopy (data not shown) is also reported.

TABLE 1

| Glycan structures | | | hmLF | Bovine fetuin | tpa | porcine thyroglobulin | α1-acid glycoprotein |
|---|---|---|---|---|---|---|---|
| N-linked | high mannose | | 0 (0) | 0 (0) | 46 (47-50) | 29 (27) | 0 (0) |
| | hybrid | | 0 (0) | 0 (0) | <1 (4) | 0 (0) | 0 (0) |
| | complex | bi-antennary | 100 (100) | 20 (14) | 48 (40) | 43 (41) | 40 (40) |
| | | tri-antennary | 0 (0) | 80 (86) | 6 (6-9) | 28 (32) | 44 (42) |
| | | tetra-antennary | 0 (0) | 0 (0) | <1 (0) | 0 (0) | 16 (18) |
| O-linked | Gal-GalNAc core | | 0 (0) | 100 (100) | <1 (0) | 0 (0) | 0 (0) |
| | Gal core | | 0 (0) | 0 (0) | 0 (0) | 0 (0) | 0 (0) |
| | Gal branched epitope | | 0 (0) | 0 (0) | 0 (0) | 0 (0) | 0 (0) |
| | O-Fucose* | | no | No | yes | no | no |
| Ration of N/O linked glycans** | | | NA | 80/20 | NA | NA | NA |
| Additional Epitopes | sialylation*** | | 75 (80) | 100 (100) | 52 (50) | 60 (58) | 100 (100) |
| | fucose | core | 100 (100) | 0 (0) | 54 (50) | 71 (73) | 1-5 (7) |
| | | antennary | 30 (33) | 0 (0) | <1 (0) | 0 | 15 (15) |
| | Gal a (1-3) Gal | | <1 (0) | 0 (0) | <1 (0) | 13 (15) | <1 (0) |

Evidence(High mannose)={Signal(LEC3) if  (3)

Signal(LEC3)>>Signal(LEC2) and (Signal(LEC4)>0 or

Signal(LEC5)>0), 0 otherwise}

Since each lectin can provide evidence for more than one glycan, the signals are iteratively processed until the inference engine converges to the following glycan profile:
Evidence(Tri-antennary)=20%
Evidence(Tetra-antennary)=55%,
Evidence(ManHigh7-9)=25%

Thus, the output is a set of glycan descriptors and quantitative estimates of the relative abundances of each descriptor in the analyzed sample. A careful choice of lectins allows for sufficient data for fingerprint deconvolution. For example, an analysis of an array of 25 lectins produces 25 signals. The required output is commonly a set of 5-10 glycan descriptors (major glycan structures and various additional epitopes). Mathematically, this indicates a problem whose number of equations is considerably larger than the number of variables. Thus, as long as the lectin binding patterns are sufficiently unique, we can expect the fingerprint to yield a solution.

Table 1 tabulates the deconvolution of fingerprints of 5 well-characterized glycoproteins: human milk lactoferrin (hmLF), bovine fetuin, a Bowes melanoma cell line derived tissue plasminogen activator (tPA), porcine thyroglobulin, and human α1-acid glycoprotein. The interpretation is based on fingerprints obtained by direct labeling of the samples. Deconvolution of the fingerprints is by the Dempster-Shafer rule-based inference algorithm. The numbers in brackets indicate percentages of each epitope as reported in the literature and verified by mass-spectrometry analysis (data not shown). NA indicates not applicable. * indicates that due to lack of multiple standards with varying levels of O-linked fucosylation, the quantitation of this epitope was not parameterized, and thus the output only detects its existence. ** is in Interpretation of the hmLF fingerprints results in the correct glycan profile (leftmost column of Table 1). Interpretation of the fingerprints demonstrates the same overall glycan structures following removal of sialic acid, galactose and GlcNAc, and detects the removal of sialic acid and appearance of terminal GlcNAc. Bovine fetuin contains 3 N-linked glycosylation sites, invariably occupied, and 3 partially occupied O-linked glycosylation sites (Green et al. J Biol. Chem. 1988; 263(34):18253-68; Edge and Spiro, J Biol. Chem. 1987; 262(33):16135-41; Spiro and Bhoyroo, J Biol. Chem. 1974; 249(18):5704-17; Yet et al. J Biol. Chem. 1988; 263 (1):111-7). Approximately 80% of the glycans are N-linked complex glycans, and the remaining 20% are O-linked. Interpretation of fetuin fingerprints results in the correct identification of the structures of both the N- and O-linked glycans, and their relative abundance (N- and O-linked glycans each calculated separately in accordance with convention, and their relative abundance is estimated from the relative intensities of lectins that preferentially recognize either N- or O-linked glycans).

Tissue plasminogen activator (tPA) (Pohl et al. Biochemistry. 1984; 23(16):3701-7; Jaques et al. Biochem J. 1996; 316 (Pt 2):427-37; Chan et al. Glycobiology. 1991 March; 1(2):173-85) contains 3 N-linked glycosylation sites, 2 of which are fully occupied, one invariably by a high-mannose glycan and the other by a complex glycan. The third site shows partial occupancy by an additional complex glycan. In the sample analyzed (derived from a Bowes melanoma cell-line) the level of occupancy of the third site is low, as deduced from the abundance of the high-mannose glycans. In addition, an O-linked fucose is present. This demonstrates that the profiling of the tPA glycans is accurate, and includes the detection of the O-linked fucose, which cannot be readily detected using standard mass-spectrometry methods. Porcine thyroglobulin (Ronin et al. J Biol. Chem. 1986; 261(16):7287-93; de Waard et al. J Biol. Chem. 1991; 266(7):4237-43; Spiro and Bhoyroo, J Biol. Chem. 1984; 259(15):9858-66) contains, in addition to the major structures detailed in Table 1, low levels of Galα(1-3)Gal, an epitope produced by all mammalians excluding higher primates and man, and which is highly antigenic in humans. The detection of this epitope and its quantification are important to manufacturers of biological therapeutics. The UC-FINGERPRINT™ technology correctly detects the level of this epitope. α1-acid glycoprotein (Sei et al. J Chromatogr A. 2002; 958(1-2):273-81) contains bi-, tri- and tetra-antennary glycans. The ability of the fingerprint to resolve the antennarity of these is evident from the accurate estimations—all within 10% of those obtained by chromatographic and mass spectroscopy techniques.

Example 3

Comparison of Glycomolecule Fingerprints Obtained Using Direct-Labeled Glycomolecules and Glycomolecule Fingerprints Obtained Using Labeled Lectins as Second Saccharide-Binding Agents Fingerprint patterns obtained using direct labeling of the samples were compared to fingerprint patterns obtained using a labeled lectin to detect glycomolecules bound to a substrate.

Figure 2A:
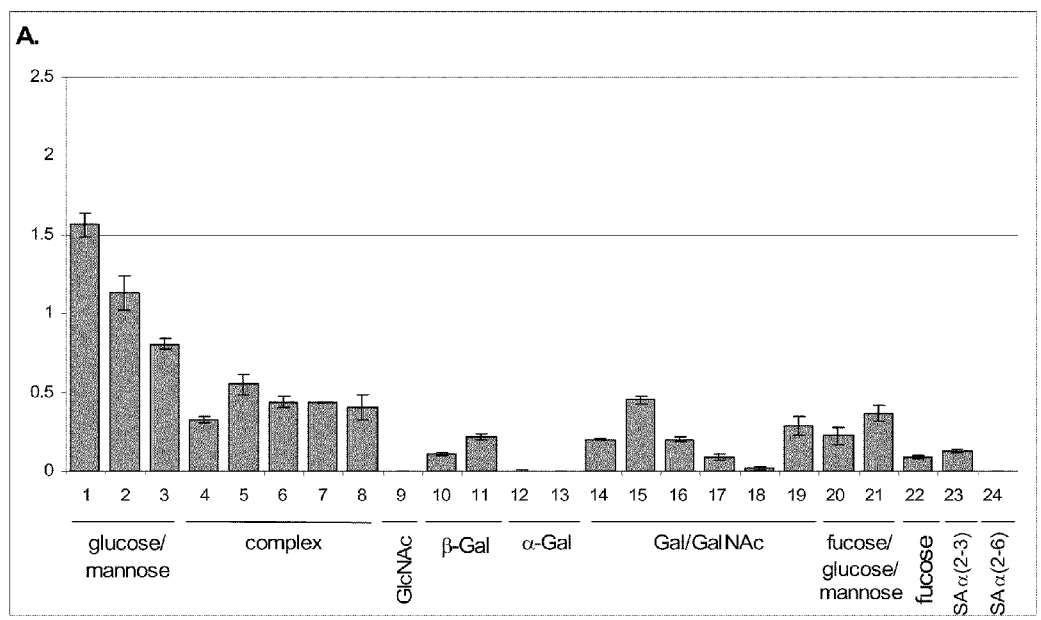
FIG. 2A-2C are fingerprints of a Bows melanoma cell-line derived tissue plasminogen activator (tPA). The fingerprint obtained in FIG. 2A was obtained using direct labeling of the sample. The fingerprint obtained in FIG. 2B was obtained using a glucose/mannose recognizing probe that recognizes both high-mannose and complex bi-antennary glycans. The fingerprint shown in FIG. 2C was obtained using a glucose/mannose-recognizing probe that recognizes only high mannose type glycans. Since each of the fingerprints was obtained using a different probe, signals were corrected for the variation in fluorescence of the labeled probes (or sample for FIG. 2A), and for the variability in scanning parameters. Deconvolution of fingerprints obtained using lectin probes requires several fingerprints each obtained with a different probe, in order to ensure signals from all lectins. Commonly 2-4 different probes, depending on the complexity of the glycosylation pattern of the sample, are required.
Figure 2B:
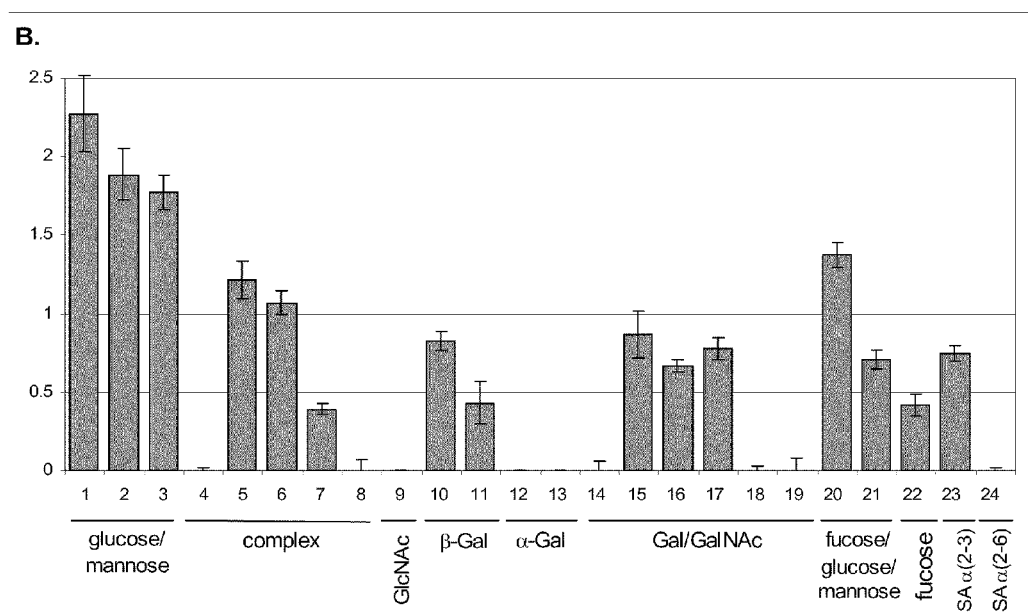
Figure 2C:
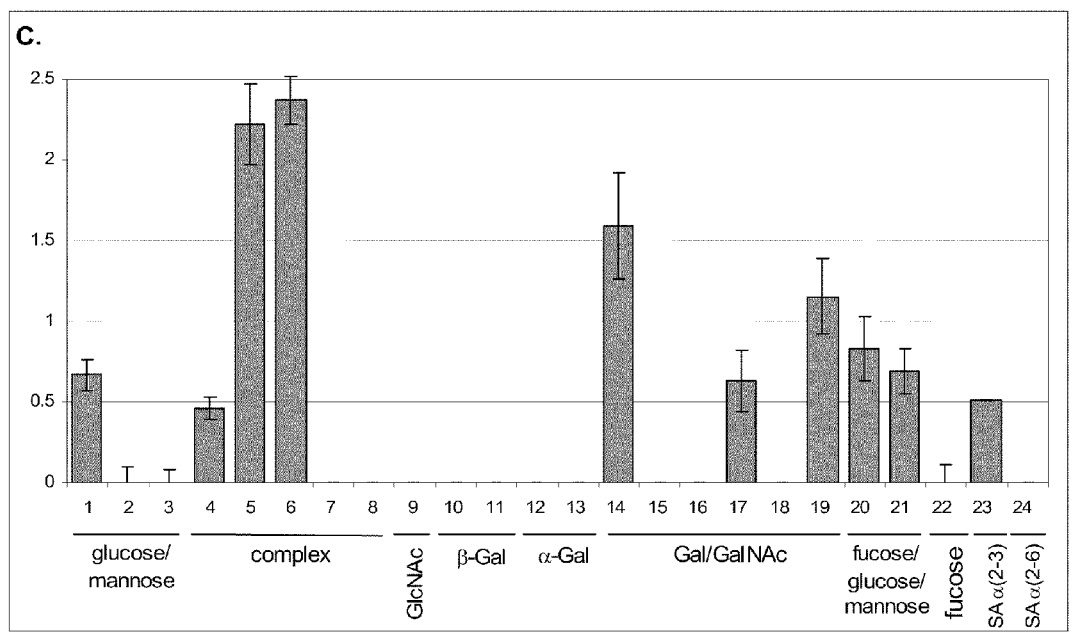

FIGS. 2A-2C shows a fingerprints of a Bows melanoma cell-line derived tissue plasminogen activator (tPA). Fingerprints were obtained by direct labeling of the sample (FIG. 2A); labeling with a glucose/mannose recognizing lectin probe that recognizes both high-mannose and complex bi-antennary glycans (FIG. 2B); or with a glucose/mannose recognizing lectin probe that recognizes only high mannose type glycans (FIG. 2C). Since each of the fingerprints was obtained using a different probe, signals were corrected for the variation in fluorescence of the labeled probes (or sample, for the study shown in FIG. 2A), and for the variability in scanning parameters. Deconvolution of fingerprints obtained using lectin probes requires several fingerprints each obtained with a different probe, in order to ensure correct assessment of signals from all lectins. Commonly 2-4 different probes, depending on the complexity of the glycosylation pattern of the sample, are required.

The fingerprint in FIG. 2A showed a stronger signal than those shown in FIGS. 2B and 2C, but lower signal intensities, demonstrating the increased sensitivity and specificity obtained with a labeled probe. The fingerprint in FIG. 2A was the input for the interpretation shown in Table 1, and shows the expected signals for complex glycans, mainly of the bi-antennary type containing a core fucose, and high-mannose type glycans. The fingerprint in FIG. 1B shows fewer signals, due mainly to increased specificity. The fingerprint in FIG. 1C shows even fewer signals: those from lectins 2 and 3 are not observed in this fingerprint.

These results demonstrate the power of using lectins as probes, and reveal the existence of a single high-mannose site in tPA. The fact that no signals are observed from lectins that recognize the high-mannose type glycans indicates that the glycoforms bound to these lectins (evident in panels a and b) do not have an additional high-mannose type lectin available for interaction with the labeled probe.

Figure 3A:
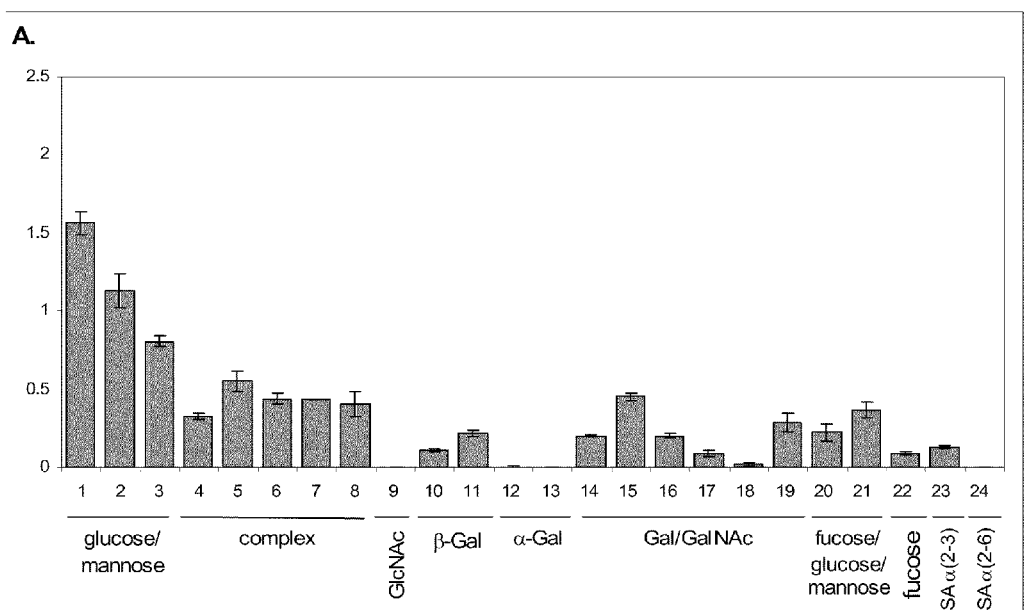
FIGS. 3A-3C are fingerprints of desialylated bovine fetuin. The fingerprint in FIG. 3A was obtained using a terminal galactose-recognizing probe. The fingerprint in FIG. 3B was obtained using a complex N-linked glycan-recognizing probe, and the fingerprint in FIG. 3C was obtained using a Gal/GalNAc recognizing probe that preferentially recognized O-linked glycans. Signal correction is same as for FIGS. 2A-2C. The high correlation between the fingerprints of panels FIG. 3A and FIG. 3B demonstrate the nearly uniform distribution of complex N-linked glycans at the three N-linked glycosylation sites; the low signals in FIG. 3C correlate to the low levels of O-linked glycans in the sample.
Figure 3B:
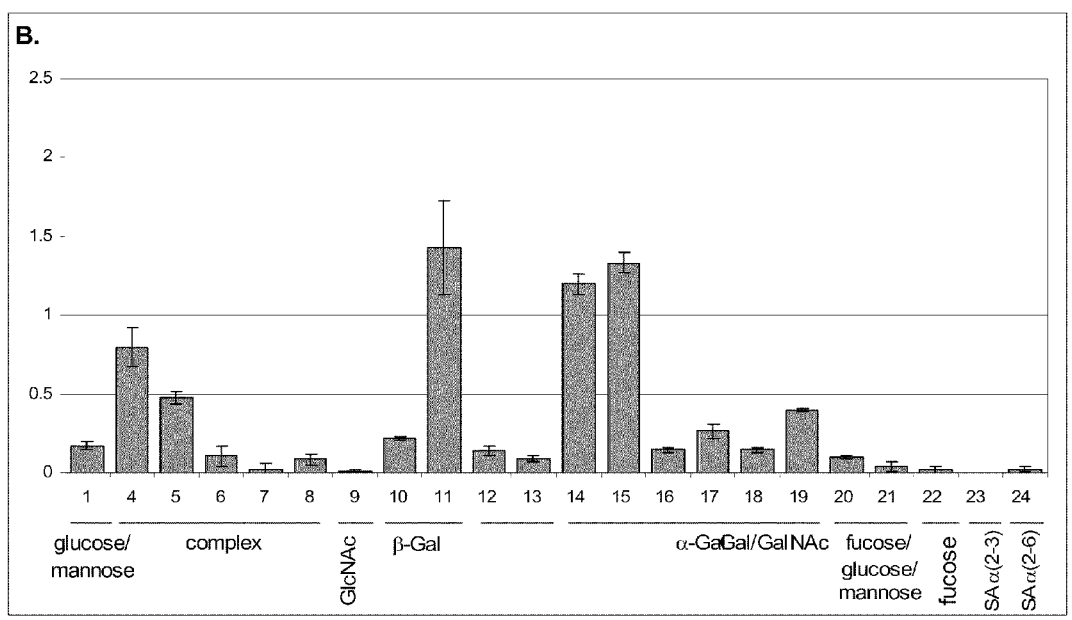
Figure 3C:
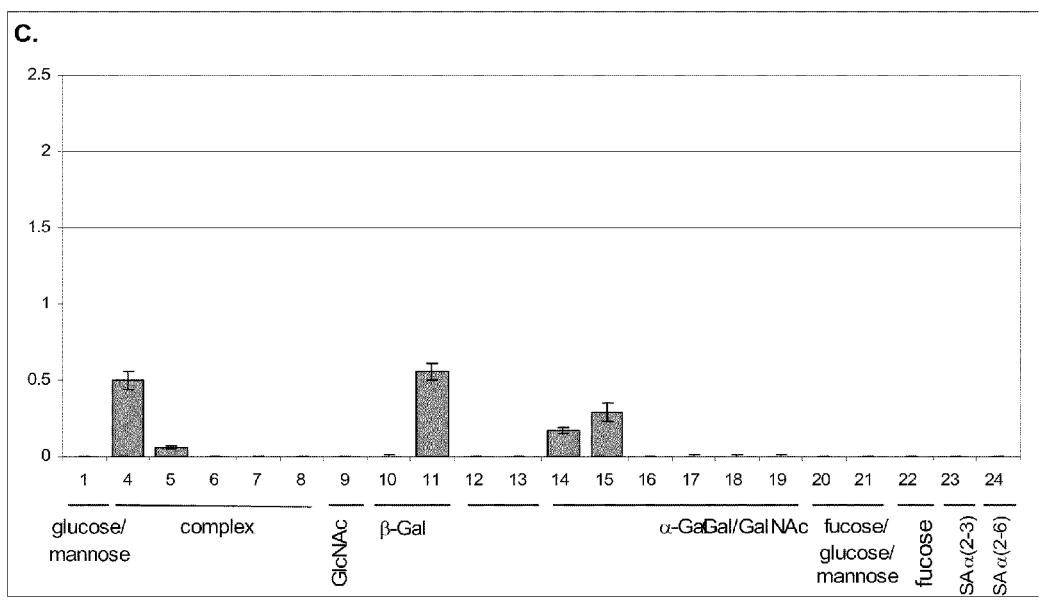

FIGS. 3A-C depicts fingerprints of de-sialylated bovine fetuin, obtained by using three probes that recognize terminal galactose (FIG. 3A), tri- and tetra antennary complex N-linked glycans (FIG. 3B), and N-acetyl-galactoseamine (GalNAc) (FIG. 3C). This latter probe preferentially recognizes O-linked glycans. Numerous lectins are sensitive to the presence of sialic acid (Yim et al. Proc Natl Acad Sci USA. 2001; 98(5): 2222-2225; Tronchin et al. Infect Immun. 2002; 70(12): 6891-6895) and its removal enables increased resolution of antennarity. The high correlation between the fingerprints of panels FIGS. 3A and B suggest that the complex type N-linked glycans are nearly uniformly distributed at the three N-linked glycosylation sites, consistent with previous publications. The fingerprint obtained with the O-linked glycan recognizing probe (FIG. 3C) shows fewer and lower signals, consistent with the lower abundance of O-linked glycans on fetuin. Moreover, the complete absence of signals from the group of Gal/GalNAc recognizing lectins in this fingerprint suggests that the majority of the glycoforms have a single O-linked glycosylation site occupied, consistent with the reported ratio of N/O linked glycans in fetuin (Yim et al. Proc Natl Acad Sci USA. 2001; 98(5): 2222-2225; Tronchin et al. Infect Immun. 2002; 70(12): 6891-6895).

Example 4

Figure 4:
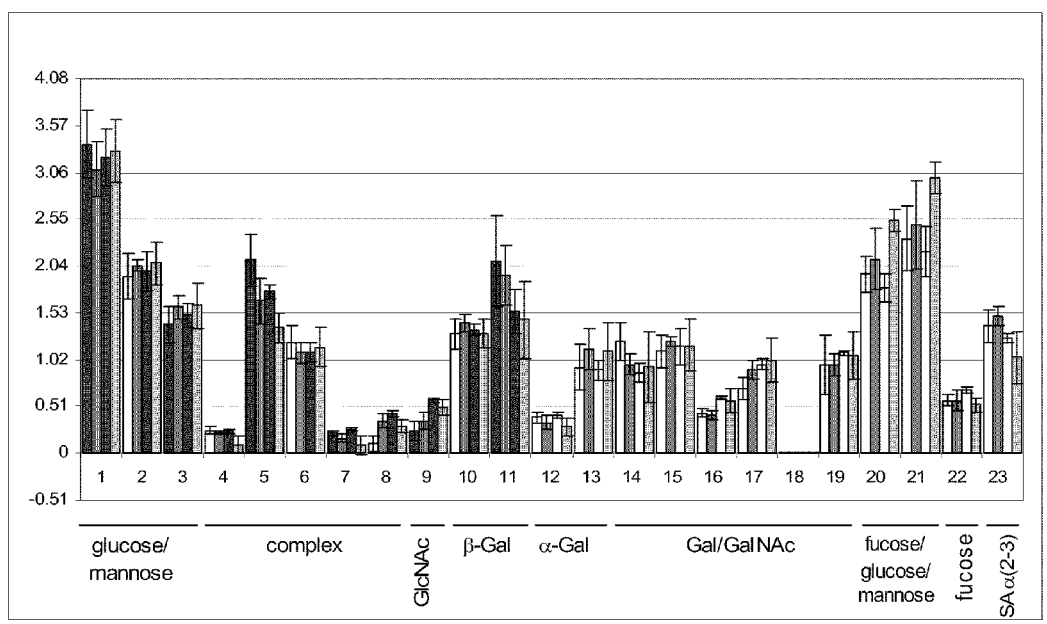
FIG. 4 shows comparisons of fingerprints of tPA from conditioned media with fingerprints from purified tPA. Fingerprints were obtained using a glucose/mannose-recognizing probe, which recognizes both the high-mannose and the bi-antennary type glycans. The fingerprints are corrected as described for FIGS. 2A-2C. cross-hatches, purified tPA; dark shading, tPA spiked into DMEM with 2% FCS collected after 48 hours of culture growth; light shading, tPA spiked into DMEM with 2% FCS after 1 week of culture growth; open, tPA spiked into DMEM with 10% FCS after 1 week of culture growth.

UC-FINGERPRINT™ Profiles Determined for Glycoproteins Obtained Directly from Conditioned Medium FIG. 4 depicts fingerprints of tPA analyzed directly in CHO-conditioned media, in comparison with a fingerprint of purified tPA. CHO cells were grown in DMEM supplemented with 2% or 10% FCS. Cell culture supernatant was collected after 48 hours or 1 week as indicated. Human tPA was spiked into the different cell culture supernatants to a final concentration of 0.7 μM. 150 μl of the tPA-containing media was collected at various time points and used for incubation with the lectin array.

The fingerprints were obtained using a glucose/mannose recognizing lectin probe. The fingerprints were comparable to the fingerprint obtained with a purified sample of the protein.

Example 5

Labeling of Small Quantities of Glycoproteins for UC-FINGERPRINT™ Profile Determination The ability of small quantities of a glycoprotein to be labeled using UC-FINGERPRINT™ technology was examined.

Figure 5:
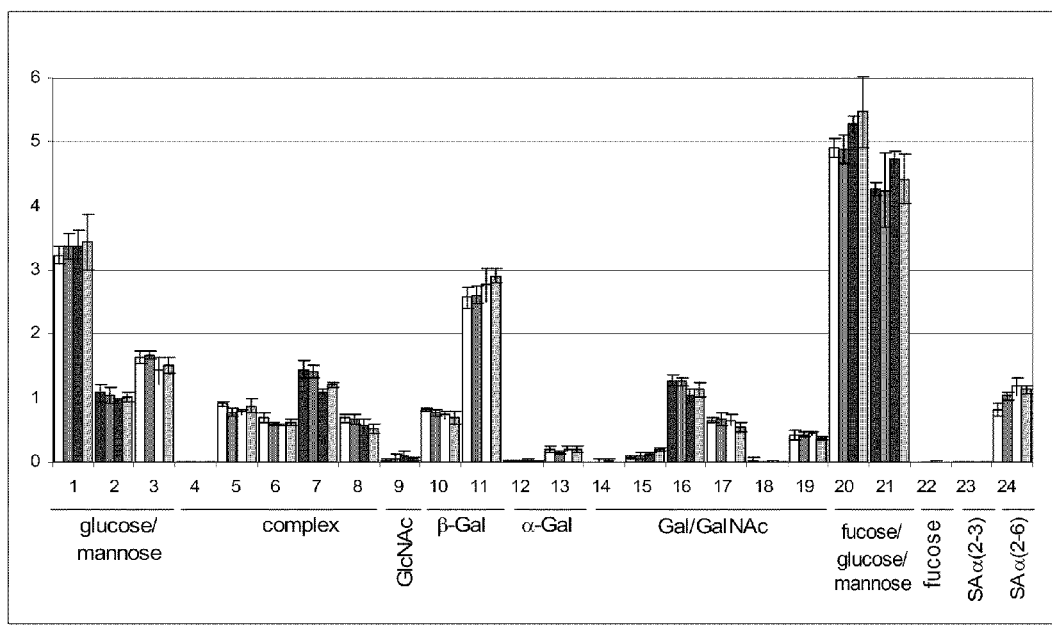
FIG. 5 shows comparisons of fingerprints of variable concentrations of human polyclonal IgG. The reduction in sample concentration demonstrates that the technology can be applied to early stages of therapeutic protein development. IgG concentrations are: 1 µM (cross-hatches); 0.7 µM (dark shading); 0.3 µM (light shading); and 0.1 µM (open).

The results are shown in FIG. 5. Shown are fingerprints of human polyclonal IgG at concentrations of 0.1 μM (clear box), 0.3 μM (light shading), 0.7 μM (dark shading), and 1 μM (diagonal lines). Fingerprints are detectable with as little as 0.1 μM of glycoproteins.

These results demonstrate that UC-FINGERPRINT™ technology can be performed with glycan structures on intact glycoproteins with minimal sample pretreatment. Thus, the method can provide a high-throughput solution for accurate analysis of protein glycosylation. The analysis can additionally be preformed on crude samples in growth media, obviating the need for time-consuming purification and degradation steps. Less than 200 μl of sample volume with protein concentrations of <0.3 μM are sufficient to produce a quantitative analysis. This renders the technology applicable to all stages of development of protein therapeutics: clone selection and optimization, process development, growth condition monitoring, manufacturing and Quality Control. Additionally, the methods can be used without purification steps, which can introduce bias into the resulting glycoform population (Bond et al. Journal of Immunological Methods, 1993; 166: 27-33).

Example 6

Fluorescein Labeling and Reduction of Desialylated Glycoprotein 0.667 µg/µl of Fc-Chimeric protein was desialized for about 16.5 hours at 37° C. in 50 mM NaAc pH 4.99, and protease inhibitor and 100 Units sialidase. The desialylated protein was then labeled at 25° C. for 2 hours with agitation in the absence of light in a volume of 500 µl at a concentration of about 0.667 µg/µl. The reaction included 80 µl 0.2M 2M $K_2HPO_4$ pH 9.18 and 21.5 µg/µl Flourescein (2 mg/ml in DMSO).

The desialylated, labeled FC-chimeric protein was made 0.2M Tris-Cl pH 8.0 and 1 mM DDT and incubated for 10 minutes at 80° C. Iodoacetic acid was then added to a final concentration of 22 mM.

Free sialic acid, fluorescein, DDT, and iodoacetic acid were removed by DG-10 chromatography. Labeling of the protein was confirmed by measuring absorbance at 280 nm and 495 nm was measured for various collected fractions.

Example 7

PNGase Treatment of Glycoproteins for UC-FINGERPRINT™ Profile Determination

The UC-FINGERPRINT™ profile of PNGase treated native or denatured erythropoietin (EPO) was determined. Denatured EPO was prepared using SDS and β-mercaptoethanol and heating to 100° C. for 10 minutes. After cooling, Triton 1% was added along with PNGaseF (0.5 U/µl).

UC-FINGERPRINT™ profiles on multiple lectins were prepared for native and denatured EPO, and for PNGaseF-treated native and denatured EPO. The fingerprints obtained for each were distinct, demonstrating that denaturing the protein and subjecting the protein to PNGase F treatment reveals glycan information for EPO that is not detected when native, denatured EPO is used.

The descriptions given are intended to exemplify, but not limit, the scope of the invention. Additional embodiments are within the claims.

What is claimed is:

1. A method for determining a glycomolecule fingerprint for a glycomolecule having glycans that are difficult to access, the method comprising:
   providing a glycomolecule, wherein the glycomolecule has been modified by removal of a plurality of sialic acid residues, wherein less than all of the sialic acid residues have been removed from the glycomolecule, and desialylation is effected by reacting the glycomolecule with a sialidase such that the glycan is made accessible;
   adding the glycomolecule to a substrate comprising an array of a plurality of saccharide-binding agents;
   detecting glycomolecule bound to saccharide-binding agents in the plurality; and
   obtaining a fingerprint for the glycomolecule based on the binding of the glycomolecule to the saccharide-binding agents.

2. The method of claim 1, wherein said glycomolecule has been further modified by treatment with N-Glycosidase F (PNGaseF).

3. The method of claim 2, wherein substantially all of the sialic acid residues have been removed from said glycomolecule.

4. The method of claim 1, wherein said glycomolecule is reacted with said sialidase in the presence of a protease inhibitor.

5. The method of claim 2, wherein substantially all of Asn-acetylglucosamine bonds have been cleaved in said glycomolecule by said PNGaseF.

6. The method of claim 1, further comprising reacting said glycomolecule with a reducing agent and an alkylating agent prior to obtaining said fingerprint.

7. The method of claim 6, wherein said method comprises reacting said glycomolecule with said reducing agent and alkylating agent following desialylation.

8. The method of claim 6, wherein said reducing agent is selected from the group consisting of β-mercaptoethanol, dithiothreitol, and mercaptethylamine.

9. The method of claim 6, wherein said alkylating agent is selected from the group consisting of iodoacetamide and iodoacetic acid.

10. The method of claim 1, wherein all steps of said method are performed in a single container.

11. The method of claim 1, wherein said glycomolecule is detected with a label associated with said glycomolecule.

12. The method of claim 11, wherein said label is a fluorescent label.

13. The method of claim 12, wherein said fluorescent label is selected from the group consisting of fluorescein isothiocyanate (FITC), rhodamine, Texas Red, and Cy5.

14. The method of claim 11, wherein said label is added to said glycomolecule prior to adding said glycomolecule to said substrate.

15. The method of claim 11, wherein said label is added to glycomolecule after adding said glycomolecule to said substrate.

16. The method of claim 11, wherein said label is added to glycomolecule while adding said glycomolecule to said substrate.

17. The method of claim 11, wherein said label is associated with a second saccharide-binding agent that binds to said glycomolecule.

18. The method of claim 17, wherein said second saccharide-binding agent is a lectin or an antibody.

19. The method of claim 1, further comprising purifying said glycomolecule prior to adding said glycomolecule to said substrate.

20. The method of claim 19, wherein said purification is by column chromatography.

21. The method of claim 1, wherein said glycomolecule is a glycoprotein.

22. The method of claim 21, wherein said glycoprotein is from a cell culture medium.

23. The method of claim 21, wherein said glycoprotein includes at least a portion of an immunoglobulin polypeptide.

24. The method of claim 23, wherein said immunoglobulin in IgG isotype.

25. The method of claim 23, wherein said portion comprises an Fc molecule.

26. The method of claim 1, wherein said method comprises treating said glycomolecule with a detergent prior to obtaining said fingerprint.

27. The method of claim 26, wherein said detergent is an ionic detergent.

28. The method of claim 27, wherein said detergent is sodium docecyl sulfate (SDS).

29. The method of claim 1, wherein said substrate is a microsphere.

30. The method of claim 29, wherein said substrate comprises a plurality of micropsheres.

31. The method of claim 29, wherein said microsphere comprises one type of saccharide-binding agent.

32. The method of claim 29, wherein said microsphere comprises more than one type of saccharide-binding agent.

33. The method of claim 11, wherein said glycomolecule is associated with a label, and bound glycomolecules are detected by identifying bound label on said substrate.

34. The method of claim 33, wherein said label is associated with an agent that binds to a non-carbohydrate molecule on said glycomolecule.

35. The method of claim 34, wherein said glycomolecule is a glycoprotein and said agent binds to a peptide epitope on said glycoprotein.

36. The method of claim 34, wherein said agent is an antibody.

37. The method of claim 11, wherein said substrate is substantially planar.

\* \* \* \* \*